United States Patent [19]
Imperante et al.

[11] Patent Number: 5,374,759
[45] Date of Patent: Dec. 20, 1994

[54] SILICONE ESTERS OF HYDROXY ACID

[75] Inventors: John Imperante, Lebanon, N.J.; Anthony J. O'Lenick, Jr., Lilburn, Ga.

[73] Assignees: Siltech Inc., Norcross, Ga.; Phoenix Chem., Somerville, N.J.

[21] Appl. No.: 210,752

[22] Filed: Mar. 22, 1994

[51] Int. Cl.$^5$ ............................... C07F 7/08
[52] U.S. Cl. ..................................... 556/437
[58] Field of Search ........................ 556/437

[56] References Cited

U.S. PATENT DOCUMENTS

| | | | |
|---|---|---|---|
| 5,159,096 | 10/1992 | Austin et al. | 556/445 |
| 5,260,469 | 11/1993 | Swiatek | 556/445 |
| 5,274,156 | 12/1993 | LeGrow et al. | 556/445 |
| 5,306,838 | 4/1994 | Shioya et al. | 556/445 |

*Primary Examiner*—Paul F. Shaver

[57] ABSTRACT

The invention relates to a series of novel silicone esters of hydroxy acids. The compounds of the present invention are prepared by reacting a the hydroxyl group in a silicone polymer with a hydroxy acid selected from the group consisting of lactic acid and glycolic acid. The compounds of the present invention find use in skin care products and other personal care products.

8 Claims, No Drawings

SILICONE ESTERS OF HYDROXY ACID

BACKGROUND OF THE INVENTION

FIELD OF THE INVENTION

The present invention relates to a series of novel silicone esters prepared by the esterification reaction of a dimethicone copolyol and a hydroxy acid selected from the group consisting of lactic and glycolic acid. These materials provide outstanding skin feel and lubrication as well as emmoliency properties. The compounds of the present invention are prepared by reacting a hydroxyl containing silicone polymer, and a hydroxy acid selected from the group consisting of lactic acid and glycolic acid.

ARTS AND PRACTICES

Silicone fluids have been known to be good oily additives to cosmetic products. They are good nondurable oily materials.

They are very stable to oxidation, however, their use has been restricted to those applications where oily materials are needed.

In many applications, there is a desire for a silky skin feel. The desired molecule should have the desirable dry feel and yet have mildness and durability of silicone oils.

THE INVENTION

OBJECT OF THE INVENTION

It is the object of the present invention to provide novel silicone ester which are prepared by the esterification reaction of a hydroxy acid selected from the group consisting of lactic and glycolic acid with a dimethicone copolyol. These compounds are substantive to the skin giving a dry talc like feel to the skin, are non-irritating, and provide emmoliency properties to the skin.

It is another objective of the current invention to provide silicone hydroxy acid esters which can be used in personal care products, more specifically skin care products.

SUMMARY OF THE INVENTION

The present invention relates to novel silicone ester which is prepared by the esterification reaction of a hydroxy acid selected from the group consisting of lactic and glycolic acid with a dimethicone copolyol. The compounds by virtue of the fatty hydroxy containing ester group are provide unique skin feel and emmoliency properties to the skin when applied in a variety of personal care products.

As will become clear from the disclosure, the compounds of the present invention while having silicone present in the molecule, have unique skin feel which is a direct result of the structure. The pendant group needs to contain (a) a silicone atom linked covalently through carbon to (b) an alkoxylated portion linked covalently to (c) an ester function, linked covalently to (d) a hydroxy containing group selected from the group consisting of lactic and glycolic acid. Compounds lacking these functional parts do not give the desired dry feel and emmoliency.

The compounds of the present invention are prepared by the by the esterification reaction of a hydroxy acid selected from the group consisting of lactic and glycolic acid with a dimethicone copolyol.

The compounds of this invention are by the esterification reaction of a hydroxy acid selected from the group consisting of lactic and glycolic acid with a dimethicone copolyol. In a preferred embodiment the dimethicone is selected from the group consisting of (a) terminal dimethicone copolyols which conform to the following structure;

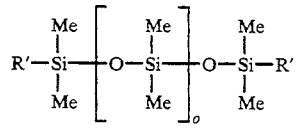

wherein;
Me is methyl;
R' is $-(CH_2)_3-O-(EO)_a-(PO)_b-(EO)_c-H$
EO is $-(CH_2CH_2-O)-$;
PO is a $-(CH_2CH(CH_3)-O)-$
o is an integer ranging from 1 to 100; and (b) comb dimethicone copolyols which conform to the following structure;

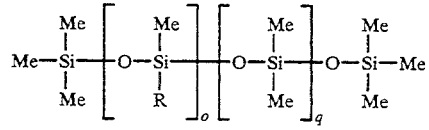

wherein;
Me is methyl;
R is $-(CH_2)_3-O-(EO)_a-(PO)_b-(EO)_c-H$
EO is $-(CH_2CH_2-O)-$;
PO is a $-(CH_2CH(CH_3)-O)-$;
o is an integer ranging from 1 to 100;
q is an integer ranging from 0 to 500.

In one preferred embodiment the compounds of the invention conform to the following structure;

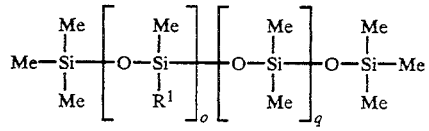

wherein;
Me is methyl;
$R^1$ is $-(CH_2)_3-O-(EO)_a-(PO)_b-(EO)_c-C(O)-R^2$
$R^2$ is selected from the group consisting of $CH_3-CH(OH)-$ and $HO-CH_2-$;
o is an integer ranging from 1 to 100;
EO is $-(CH_2CH_2-O)-$;
PO is a $-(CH_2CH(CH_3)-O)-$.

In another preferred embodiment the compounds of the invention conform to the following structure;

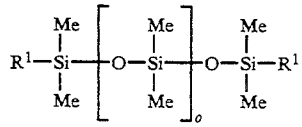

wherein;

$R^1$ is —$(CH_2)_3$—O—$(EO)_a$—$(PO)_b$—$(EO)_c$—C(O)—$R^2$ $R^2$ is selected from the group consisting of $CH_3$—CH(OH)— and HO—$CH_2$—;

Me is methyl;

EO is —($CH_2CH_2$—O—);

PO is a —($CH_2CH(CH_3)$—O)— o is an integer ranging from 1 to 100;

$R^1$ is —$(CH_2)_3$—O—$(EO)_a$—$(PO)_b$—$(EO)_c$—C(O)—$R^2$ $R^2$ is selected from the group consisting of $CH_3$—CH(OH)— and HO—$CH_2$—.

EXAMPLES

The compounds of the present invention are prepared by the reaction of a hydroxy silicone compound and an anhydride. Examples of suitable reactants are as follows;

REACTANTS

Hydroxy Acids

The hydroxy acids useful as raw materials for the preparation of the compounds of the present invention are commercially available. They are;

| Lactic Acid | $CH_3$—CH(OH)C(O)—OH |
|---|---|
| Glycolic Acid | HO—$CH_2$—C(O)—OH |

Hydroxy Silicone Compounds

Many manufacturers offer a series of hydroxy silicone compounds suitable for use as raw materials in the preparation of the esters of the present invention. These materials are marketed under the many trade names. Siltech Inc, Union Carbide, Dow Corning, Mazer and many other manufacturers also offer the compounds commercially.

The preferred method of placing this type of reactive hydroxyl group into the silicone polymer is by the reaction of silanic hydrogen containing polymer with allyl alcohol alkoxylates. This technology is well known to those skilled in the art and are described in U.S. Pat. No. 4,083,856. These hydroxyl functional silicone compounds are subsequently reacted with hydroxy acids, to make the compounds of the present invention.

Additionally, hydroxy silicone compounds are available from Siltech Inc. Norcross Ga. These compounds conform to the following generic structure;

$$\text{Me}-\underset{\text{Me}}{\overset{\text{Me}}{\underset{|}{\text{Si}}}}-\left[\text{O}-\underset{R^5}{\overset{\text{Me}}{\underset{|}{\text{Si}}}}\right]_o-\left[\text{O}-\underset{R^1}{\overset{\text{Me}}{\underset{|}{\text{Si}}}}\right]_q-\text{O}-\underset{\text{Me}}{\overset{\text{Me}}{\underset{|}{\text{Si}}}}-\text{Me}$$

wherein;

Me is methyl;

$R^5$ is —$(CH_2)_3$—O—$(EO)_a$—$(PO)_b$—$(EO)_c$—H $R^1$ is selected from lower alkyl $CH_3(CH)_n$— or phenyl;

n is an integer from 0 to 8;

a, b and c are integers independently ranging from 0 to 20;

EO is an ethylene oxide residue —($CH_2CH_2$—O)—;

PO is a propylene oxide residue —($CH_2CH(CH_3)$—O)—;

o is an integer ranging from 1 to 100;

q is an integer ranging from 0 to 500.

| Example | Name | a | b | c | o | q |
|---|---|---|---|---|---|---|
| 1 | Siltech H 1000 | 3 | 0 | 0 | 2 | 54 |
| 2 | Siltech H 1100 | 10 | 5 | 10 | 10 | 100 |
| 3 | Siltech H 1200 | 20 | 20 | 20 | 2 | 56 |
| 4 | Siltech H 1300 | 10 | 10 | 10 | 6 | 26 |
| 5 | Siltech H 1400 | 0 | 10 | 0 | 4 | 200 |
| 6 | Siltech H 1500 | 5 | 5 | 5 | 2 | 50 |
| 7 | Siltech H 1600 | 0 | 6 | 0 | 10 | 25 |
| 8 | Siltech H 1700 | 0 | 0 | 0 | 5 | 10 |

Terminal Substituted Dimethicone Copolyol Compounds

Terminal substituted dimethicone copolyol compounds are well known and are marketed in the trade under many names.

The preferred method of placing this type of reactive hydroxyl group into the silicone polymer is by the reaction of terminal silanic hydrogen containing polymer with allyl alcohol alkoxylates. This technology is well known to those skilled in the art and are described in U.S. Pat. No. 4,083,856.

These materials are available from Siltech Inc. Norcross Ga. and are marketed under the Siltech T series trade name.

$$R^6-\underset{\text{Me}}{\overset{\text{Me}}{\underset{|}{\text{Si}}}}-\left[\text{O}-\underset{\text{Me}}{\overset{\text{Me}}{\underset{|}{\text{Si}}}}\right]_o-\left[\text{O}-\underset{R^1}{\overset{\text{Me}}{\underset{|}{\text{Si}}}}\right]_q-\text{O}-\underset{\text{Me}}{\overset{\text{Me}}{\underset{|}{\text{Si}}}}-R^6$$

wherein;

Me is methyl;

$R^6$ is —$(CH_2)_3$—O—$(EO)_a$—$(PO)_b$—$(EO)_c$—H $R^1$ is selected from lower alkyl $CH_3(CH)_n$— or phenyl;

n is an integer from 0 to 8;

a, b and c are integers independently ranging from 0 to 20;

EO is an ethylene oxide residue —($CH_2CH_2$—O)—;

PO is a propylene oxide residue —($CH_2CH(CH_3)$—O)—;

o is an integer ranging from 1 to 100;

q is an integer ranging from 0 to 500.

| Example | Name | a | b | c | Equivalent Molecular Weight |
|---|---|---|---|---|---|
| 9 | Siltech T 701 | 0 | 0 | 0 | 1,000 |
| 10 | Siltech T 706 | 5 | 1 | 0 | 6,000 |
| 11 | Siltech T 710 | 2 | 1 | 1 | 10,000 |
| 12 | Siltech T 750 | 10 | 5 | 10 | 50,000 |
| 13 | Siltech T 790 | 20 | 20 | 20 | 86,000 |

General Reaction Conditions

The reaction can be run with either a stiochiometric amount of the hydroxy acid or with an excess of silicone polymer. The esterification can be carried out without catalyst; however, when no catalysts are used reaction rates are less efficient. Standard esterification catalysts are generally used at concentrations of between 0.05% to 0.50% with a preferred range of 0.1% to 0.3%. Catalysts which are effective include but are not limited to; sulfuric acid, p-toluene sulfonic acid, methane sulfonic acid, tin metal, zinc metal, titanium metal, organo titianates, organo tin compounds, organo zinc compounds, zinc oxide, magnesium oxide, calcium oxide, etc.. The most preferred catalyst is stannous oxylate. The reaction is conducted at between 140 and 240 C. under an inert nitrogen blanket. The nitrogen blanket preserves the color. Preferred temperature range is between 180 and 210 C. Water is removed from the reaction which is done using a nitrogen sparge or vacuum.

Example 14

Into a suitable round bottom, three neck flask equipped with a thermometer and a nitrogen sparge is added 1,000 grams of the silicone compound example 1 and the 90.0 grams of lactic acid. The reaction mass is blanketed with nitrogen, and heated to 180 and 210 C. under the inert nitrogen blanket.

Water is distilled off. Within four to five hours the acid value is vanishingly low. The product is a clear liquid and is used without additional purification.

Examples 15–32

Example 14 is repeated only this time substituting the specified number of grams of the specified hydroxy acid and the specified type and number of grams of silicone compound as shown below;

| Example | Hydroxy Acid | Grams | Silicone Reactant Example | Grams |
|---|---|---|---|---|
| 15 | Lactic | 90.0 | 1 | 2,329.0 |
| 16 | Lactic | 90.0 | 2 | 2,032.0 |
| 17 | Lactic | 90.0 | 3 | 5,129.0 |
| 18 | Lactic | 90.0 | 4 | 347.6 |
| 19 | Lactic | 90.0 | 5 | 4,407.0 |
| 20 | Lactic | 90.0 | 6 | 2,743.0 |
| 21 | Lactic | 90.0 | 7 | 3,550.8 |
| 22 | Lactic | 90.0 | 8 | 1,512.4 |
| 23 | Lactic | 90.0 | 9 | 1,000.0 |
| 24 | Lactic | 90.0 | 10 | 6,000.0 |
| 25 | Lactic | 90.0 | 11 | 10,000.0 |
| 26 | Lactic | 90.0 | 12 | 50,000.0 |
| 27 | Lactic | 90.0 | 13 | 86,000.0 |
| 28 | Glycolic | 76.0 | 1 | 2,329.0 |
| 29 | Glycolic | 76.0 | 2 | 2,032.0 |
| 30 | Glycolic | 76.0 | 3 | 5,129.0 |
| 31 | Glycolic | 76.0 | 4 | 347.6 |
| 32 | Glycolic | 76.0 | 5 | 4,407.0 |
| 33 | Glycolic | 76.0 | 6 | 2,743.0 |
| 34 | Glycolic | 76.0 | 7 | 3,550.8 |
| 35 | Glycolic | 76.0 | 8 | 1,512.4 |
| 36 | Glycolic | 76.0 | 9 | 1,000.0 |
| 37 | Glycolic | 76.0 | 10 | 6,000.0 |
| 38 | Glycolic | 76.0 | 11 | 10,000.0 |
| 39 | Glycolic | 76.0 | 12 | 50,000.0 |
| 40 | Glycolic | 76.0 | 13 | 86,000.0 |
| 41 | Lactic | 45.0 | 1 | 2,329.0 |
| 42 | Lactic | 45.0 | 2 | 2,032.0 |
| 43 | Lactic | 45.0 | 3 | 5,129.0 |
| 44 | Lactic | 45.0 | 4 | 347.6 |
| 45 | Lactic | 45.0 | 5 | 4,407.0 |
| 46 | Lactic | 45.0 | 6 | 2,743.0 |
| 47 | Lactic | 45.0 | 7 | 3,550.8 |
| 48 | Lactic | 45.0 | 8 | 1,512.4 |
| 49 | Lactic | 45.0 | 9 | 1,000.0 |
| 50 | Lactic | 45.0 | 10 | 6,000.0 |
| 51 | Lactic | 45.0 | 11 | 10,000.0 |
| 52 | Lactic | 45.0 | 12 | 50,000.0 |
| 53 | Lactic | 45.0 | 13 | 86,000.0 |
| 54 | Glycolic | 36.0 | 1 | 2,329.0 |
| 55 | Glycolic | 36.0 | 2 | 2,032.0 |
| 56 | Glycolic | 36.0 | 3 | 5,129.0 |
| 57 | Glycolic | 36.0 | 4 | 347.6 |
| 58 | Glycolic | 36.0 | 5 | 4,407.0 |
| 59 | Glycolic | 36.0 | 6 | 2,743.0 |
| 60 | Glycolic | 36.0 | 7 | 3,550.8 |
| 61 | Glycolic | 36.0 | 8 | 1,512.4 |
| 62 | Glycolic | 36.0 | 9 | 1,000.0 |
| 63 | Glycolic | 36.0 | 10 | 6,000.0 |
| 64 | Glycolic | 36.0 | 11 | 10,000.0 |
| 65 | Glycolic | 36.0 | 12 | 50,000.0 |
| 66 | Glycolic | 36.0 | 13 | 86,000.0 |

The compounds of the present invention were found to have a silky talc like feel when applied to skin. They have been found to have low toxicity when applied to the skin and eyes, and non-toxic when ingested.

What is claimed:

1. A silicone ester prepared by the esterification reaction of a hydroxy acid selected from the group consisting of lactic and glycolic acid with a dimethicone copolyol.

2. A compound of claim 1 wherein the dimethicone is selected from the group consisting of
   (a) terminal dimethicone copolyols which conform to the following structure;

$$R'-\underset{\underset{Me}{|}}{\overset{\overset{Me}{|}}{Si}}-\left[O-\underset{\underset{Me}{|}}{\overset{\overset{Me}{|}}{Si}}\right]_o-O-\underset{\underset{Me}{|}}{\overset{\overset{Me}{|}}{Si}}-R'$$

wherein;
Me is methyl;
R' is —(CH$_2$)$_3$—O—(EO)$_a$—(PO)$_b$—(EO)$_c$—H
EO is —(CH$_2$CH$_2$—O)—;
PO is a —(CH$_2$CH(CH$_3$)—O)—
is an integer ranging from 0 to 20;
b is an integer ranging from 0 to 20;
c is an integer ranging from 0 to 20;
o is an integer ranging from 1 to 100; and (b) comb dimethicone copolyols which conform to the following structure;

$$Me-\underset{\underset{Me}{|}}{\overset{\overset{Me}{|}}{Si}}-\left[O-\underset{\underset{R}{|}}{\overset{\overset{Me}{|}}{Si}}\right]_o\left[O-\underset{\underset{Me}{|}}{\overset{\overset{Me}{|}}{Si}}\right]_q-O-\underset{\underset{Me}{|}}{\overset{\overset{Me}{|}}{Si}}-Me$$

wherein;
Me is methyl;
R is —(CH$_2$)$_3$—O—(EO)$_a$—(PO)$_b$—(EO)$_c$—H;
o is an integer ranging from 1 to 100;
q is an integer ranging from 0 to 500;
EO is —(CH$_2$CH$_2$—O)—;
PO is a —(CH$_2$CH(CH$_3$)—O)—;
a is an integer ranging from 0 to 20;
b is an integer ranging from 0 to 20;
c is an integer ranging from 0 to 20.

3. A silicone polymer of claim 2 wherein said dimethicone copolyol conform to the following structure;

$$R'-\underset{\underset{Me}{|}}{\overset{\overset{Me}{|}}{Si}}-\left[O-\underset{\underset{Me}{|}}{\overset{\overset{Me}{|}}{Si}}\right]_o-O-\underset{\underset{Me}{|}}{\overset{\overset{Me}{|}}{Si}}-R'$$

wherein;

Me is methyl;
R' is —(CH₂)₃—O—(EO)ₐ—(PO)ᵦ—(EO)ᵧ—H;
o is an integer ranging from 1 to 100;
EO is —(CH₂CH₂—O)—;
PO is a —(CH₂CH(CH₃)—O)—;
a is an integer ranging from 0 to 20;
b is an integer ranging from 0 to 20;
c is an integer ranging from 0 to 20.

4. A silicone polymer of claim 2 wherein said dimethicone copolyol conform to the following structure;

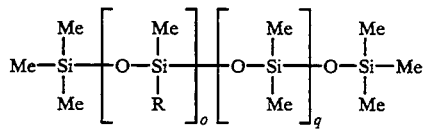

wherein;
Me is methyl;
R is —(CH₂)₃—O—(EO)ₐ—(PO)ᵦ—(EO)ᵧ—H;
o is an integer ranging from 1 to 100;
q is an integer ranging from 0 to 500;
EO is —(CH₂CH₂—O)—;
PO is a —(CH₂CH(CH₃)—O)—;
a is an integer ranging from 0 to 20;
b is an integer ranging from 0 to 20;
c is an integer ranging from 0 to 20.

5. A silicone polymer of claim 3 in which $R^2$ is $CH_3$—CH(OH)—.

6. A silicone polymer of claim 3 wherein $R^2$ is HO—CH₂—.

7. A silicon polymer of claim 4 in which $R^2$ is

8. A silicone polymer of claim 4 wherein $R^2$ is HO—CH₂—.

* * * * *